US008569570B2

(12) United States Patent
Tamburro et al.

(10) Patent No.: US 8,569,570 B2
(45) Date of Patent: Oct. 29, 2013

(54) AIRLAID SHEET MATERIAL

(75) Inventors: Maurizio Tamburro, Chieti (IT); Giovanni Carlucci, Chieti (IT)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 13/471,694

(22) Filed: May 15, 2012

(65) Prior Publication Data
US 2012/0296302 A1 Nov. 22, 2012

(30) Foreign Application Priority Data
May 16, 2011 (EP) .................................... 11166291

(51) Int. Cl.
*A61F 13/15* (2006.01)
(52) U.S. Cl.
USPC .................. 604/373; 428/195.1; 427/2.31
(58) Field of Classification Search
USPC .............. 604/367, 368, 370, 373; 428/195.1; 264/112, 113; 156/62.2, 277; 523/105; 427/2.31, 208
See application file for complete search history.

(56) References Cited

U.S. PATENT DOCUMENTS

| 3,380,851 A | 4/1968 | Lindemann et al. |
| 4,614,679 A | 9/1986 | Farrington, Jr. et al. |
| 5,021,529 A | 6/1991 | Garrett |
| 5,128,082 A * | 7/1992 | Makoui .......................... 264/112 |
| 5,607,414 A | 3/1997 | Richards et al. |
| H1698 H | 11/1997 | Lloyd et al. |
| 2002/0169430 A1 | 11/2002 | Kirk et al. |
| 2003/0003830 A1 | 1/2003 | Ouederni et al. |
| 2003/0089443 A1 | 5/2003 | Ouederni et al. |
| 2003/0130633 A1 | 7/2003 | Graef et al. |
| 2004/0123963 A1 | 7/2004 | Chen et al. |
| 2004/0170813 A1 * | 9/2004 | Digiacomantonio et al. .......................... 428/195.1 |
| 2006/0004335 A1 | 1/2006 | Wang et al. |

FOREIGN PATENT DOCUMENTS

| DE | 10218259 A1 | 11/2003 |
| EP | 337 296 A2 | 10/1989 |
| EP | 0 850 615 A1 | 7/1998 |
| EP | 085615 A1 | 7/1998 |
| EP | 1 800 638 A1 | 6/2007 |
| EP | 1 811 071 A1 | 7/2007 |
| GB | 2191779 A | 12/1987 |
| WO | WO 98/28478 | 7/1998 |
| WO | WO 98/28478 A1 | 7/1998 |
| WO | WO 00/74620 A1 | 12/2000 |

OTHER PUBLICATIONS

International Search Report, mailed Jun. 29, 2012, 4 pages.
PCT Search Report, mailed Jun. 29, 2012, 9 pages.

* cited by examiner

*Primary Examiner* — Melanie Hand
(74) *Attorney, Agent, or Firm* — Andres E. Velarde; Brian M. Bolam

(57) ABSTRACT

The present invention relates to an airlaid sheet material comprising a dry laid fibrous web and a latex coating on both surfaces thereof in selected amounts. The airlaid sheet material can be an absorbent structure for absorption of fluids.

9 Claims, 1 Drawing Sheet

AIRLAID SHEET MATERIAL

FIELD OF THE INVENTION

The present invention relates to airlaid fibrous sheet materials for absorbing fluids. The sheet materials are bonded by application of a liquid binder; they are particularly suitable for use in disposable absorbent articles.

BACKGROUND OF THE INVENTION

Fibrous sheet materials, particularly fibrous sheet materials for absorbing fluids, are manufactured for many uses, for example they are incorporated into absorbent articles such as disposable diapers, incontinent pads and catarnenial napkins as fluid absorption or fluid transmission and/or diffusion elements, for example, as absorbent cores that are intended to absorb and retain body fluids. Fibrous sheet materials, and more specifically fibrous sheet materials used to absorbem articles as fluid absorption or fluid transmission and/or diffusion elements, usually comprise a multiplicity of components so as to improve their specific performances; further components can be also included to provide the structure with added benefits.

Dry laying and, more specifically, air laying processes are widely used to produce webs from dry fibres, which can in turn be used e.g. as sheet materials for absorbing fluids. Particularly, the air laying process refers to the formation of webs with a random fibre orientation; the properties of such air laid webs are therefore somewhat isotropic. The fibrous sheet materials produced by airlaying processes are soft, flexible and porous, and are particularly suitable for use as liquid absorbent structures in absorbent articles, such as disposable diapers, sanitary napkins, pantiliners, incontinent pads, and wipes.

The airlaying manufacturing process generally comprises a web formation and layering step and a web bonding and stabilizing step; in airlaying processes in fact the fibres, that can be of any type, e.g. cellulosic, synthetic, or any combination thereof, are formed or condensed into a web, but such web lacks integrity, and mast, therefore be stabilized. Different techniques for bonding and stabilizing a dry formed web are known in the art, i.e. mechanical, thermal and chemical bonding processes. Bonding a web structure by means of a chemical is one of the most common methods of bonding in the nonwoven industry, and consists in the application of a chemical binder to the web and in the curing of the binder. The most widely used chemical is latex, since it is cheap, versatile, easy to apply, and very effective as a binder. Several methods are known to apply the latex binder to the fibrous web, while spray bonding and print bonding am particularly preferred for fibrous webs intended to be used in absorbent articles.

The latex binder is usually an aqueous emulsion, and can be applied to one or both major flat surfaces of the fibrous web. The desired amount is measured in order to provide the structure with stability and strength, at the same time without impairing fluid handling, typically absorption and/or acquisition capacity. The latex binder in fact while binding the fibres together, also to a certain extent coats them, and can at least partially reduce the capability of the fibrous sheet material of acquiring and absorbing fluids. Also, a selected amount of latex which may be optimal in order to provide the airlaid sheet material with the desired stability and strength may influence negatively its flexibility and softness, actually reducing it.

Hence, there still exists a need for an airlaid sheet material stabilized by means of a latex binder and capable of providing effective fluid handling combined with softness and flexibility, while at the same time also having the desired strength and stability. It has now been discovered feat this need can be addressed by an airlaid sheet material stabilized by means of a latex binder provided in a selected distribution, therefore providing an absorbent structure which is soft and has a good integrity, while also featuring improved fluid handling capability.

SUMMARY OF THE INVENTION

The present invention relates to an airlaid sheet material, obtainable by the process comprising the steps of:

providing a fibrous web comprising cellulosic fibres and synthetic fibres, and having a first surface and a second surface, and applying a latex binder to the first surface and to the second surface of die fibrous layer, respectively in a first amount and in a second amount, with a ratio of the first amount to the second amount from 2:1 to 4:1, preferably from 2.5:1 to 3.5:1, and wherein the airlaid sheet material comprises from 1% to 30% by weight, or from 1% to 20% by weight, or from 1% to 10% by weight, of the cellulosic fibres, from 1% to 25% by weight, or from 5% to 15% by weight, or from 5%; to 10% by weight, of the latex binder.

BRIEF DESCRIPTION OF THE DRAWINGS

White the specification concludes with claims particularly pointing out and distinctly claiming the present invention, it is believed that the present invention will be better understood from the following description in conjunction with the following drawings:

DETAILED DESCRIPTION OF THE INVENTION

Figure 1:
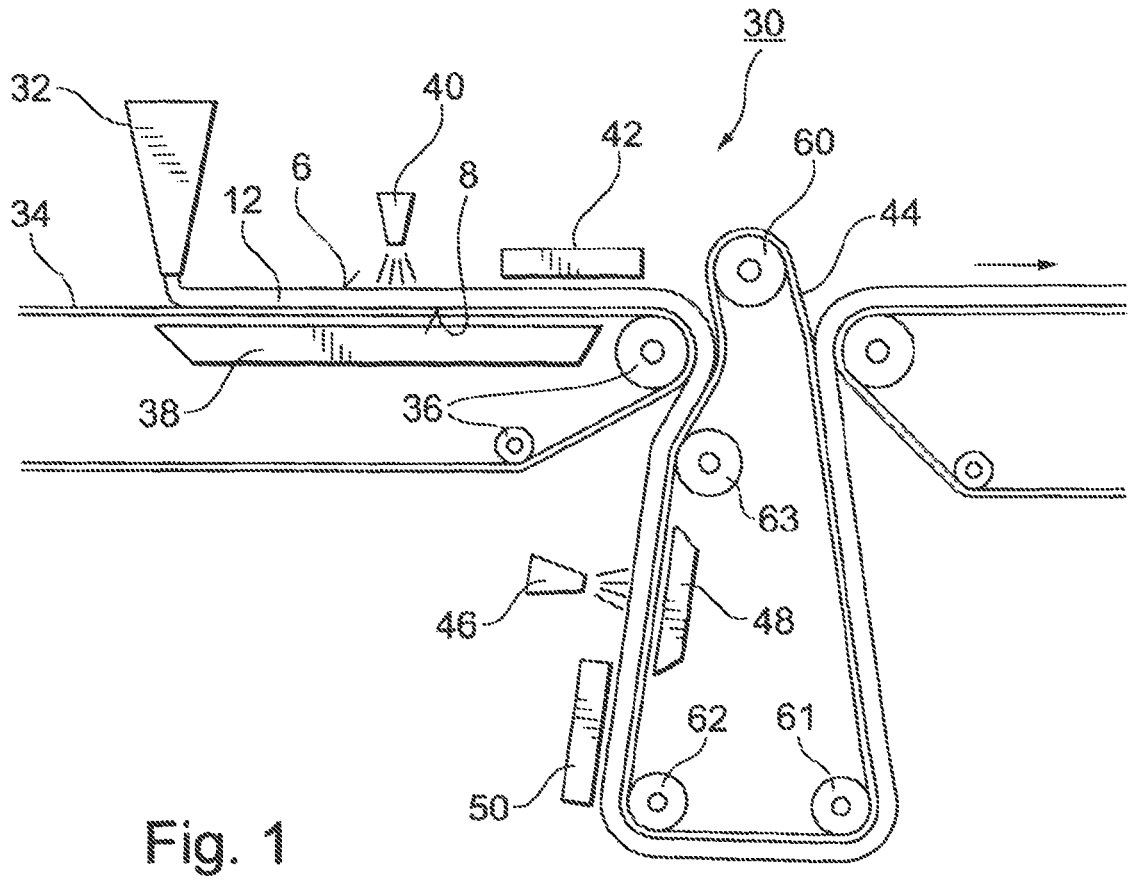
FIG. 1 is a schematic, fragmentary side elevational view of an apparatus for making an airlaid sheet material according to the present invention.

The present invention relates to a fibrous structure for absorption of fluids obtainable according to an airlaying process. The fibrous structure is constituted by an airlaid sheet material bonded by means of a latex binder, and being substantially free of superabsorbent material. In a typical embodiment, the sheet materials of the present. Invention can be incorporated as absorbent structures into absorbent articles, for example as absorbent cores, and are intended to absorb and retain the various body fluids. Absorbent articles, and more specifically disposable absorbent articles, refer to articles such as sanitary napkins, disposable diapers, incontinent pads, that are worn by a user adjacent to the body and are intended to absorb and contain the various body fluids that are discharged from the body (e.g., vaginal discharges, menses, sweat, and/or urine) and which is intended to be discarded after a single use. Absorbent articles typically comprise a body facing surface and a garment facing surface opposite thereto. A body facing surface and a garment facing surface can also be identified typically in each sheet material constituting the article itself, for example in the airlaid sheet material according to the present invention.

Disposable absorbent articles can typically comprise a fluid pervious topsheet, a fluid impervious backsheet, that can optionally be water vapour and/or gas pervious, and an absorbent element comprised therebetween.

The term "use", as used herein, refers to the period of time that starts when the absorbent article is actually put in contact with the anatomy of the user.

By saying that the airlaid sheet material of the present invention is "substantially free" of superabsorbent material, it is meant in the context of the present invention that the sheet material should not comprise any significant amount of superabsorbent material within its structure. Superabsorbent materials for use in absorbent articles typically comprise water-insoluble, water-swellable, hydrogel-forming crosslinked absorbent polymers which are capable of absorbing large quantities of liquids and of retaining such absorbed liquids under moderate pressure, and can be typically incorporated in absorbent articles in finely dispersed form, for example in particulate form. While superabsorbent material which can be present at an outer surface of the airlaid sheet material of the present invention, for example at the interface between the specified airlaid sheet material and an adjacent layer, which could be for example an outer layer wrapping the airlaid sheet material, in some cases can accidentally and slightly penetrate the structure of the specified sheet material, such shall not be considered significant. Significant amount can correspond to less than less than 5% by weight, or less than 2% by weight, or less than 1 % by weight, based ors the dry weight of the airlaid sheet material.

In general, and unless otherwise provided, all percentages by weight mentioned tor the airlaid sheet material of the present invention are calculated on the dry weight of the airlaid sheet material. The basis weights for the airlaid sheet material are also meant as dry basis weights.

The airlaid sheet material of the present invention can be made using conventional equipment designed for air laying processes.

The invention will be described as an air laid sheet material which is capable of providing effective acquisition and absorption of aqueous fluids, particularly body fluids, being for example intended to be incorporated as absorbent structure in a disposable absorbent article, e.g. a sanitary napkin.

FIG. 1 is a simplified schematic illustration of a typical embodiment of an apparatus for the manufacture of the airlaid sheet material according to the airlaying process. In accordance with this embodiment, the air forming system, indicated generally by the numeral 30, includes a distributor unit 32 disposed transversely above a continuous forming screen 34 mounted on rollers 36 and driven by a suitable motor (not shown), and vacuum means or suction box 38 is positioned beneath the screen. In a conventional air forming system, upstream of the distributor unit is a defibrator or feeder (not shown) such as a hammermill or Rando-Feeder, where bales, laps or the like are defiberized, and further the fibres may be cleaned and/or blended if necessary or desired depending largely on the type of fibres used, the blend of fibres used, and the end product sought. For example, cellulosic fibres can be blended with synthetic fibres and applied as a homogeneous blend by a single distributor. As a possible alternative, different fibres, or also different blends of fibres, can be each conveyed by a different distributor to the screen to form multiple piles or layers.

The porous forming screen 34 is essentially coextensive with the distributor or distributors, and the suction box 38 beneath the screen 34 draws the air stream downwardly and conveys the fibres to the surface of the screen thereby forming plies or a loose web 12.

According to the present invention, the fibres coming from the distributor unit 30, or alternatively the different distributors, cart be provided onto an optional preformed carrier layer, not shown in the drawings, in turn firstly provided onto the porous forming screen 34. The carrier layer can be for example a low basis weight nonwoven typically made of synthetic fibres, for example of polypropylene fibres.

At this stage in the process, the web exhibits little integrity, and the vacuum means retains the loose, fibrous web on the screen. The web 12 has a first surface 6 that faces the distributor and a second surface 8, opposite to surface 6, which faces the forming screen 34.

It should be understood that the system may be modified to control the composition and thickness of the end product. For example, the distributor unit can also comprise a plurality of individual distributors, wherein the number of distributors and their particular arrangement can be altered or varied depending on such factors as machine speed, capacity, type of fibres, and end product desired.

At this stage of the process, the web 12 collected on the forming screen 34 has very little integrity and requires stabilization. The web is advanced by the continuous screen, and if desired, the web first may be passed between compression rollers (not shown).

From them, the web is transported to a suitable first dispensing means 40, such as a spray nozzle, doctor blade, roller applicator, or the like, where a latex binder is applied to the first surface 6 of the loose web 12. A vacuum applied by the same suction box 38 positioned beneath the dispensing means and screen can also help to draw the latex into the web, if desired. The dispensing means or applicator is essentially coextensive with the width of the web, and typically a substantially uniform coating is applied to the web surface.

The latex when cured imparts integrity to the web, and therefore some penetration of the latex is typically required. The extent or degree of penetration of the latex into the web cars be controlled by controlling the amount of latex applied and by controlling the vacuum applied to the web in that the vacuum helps to draw the latex into the web. The latex can be usually applied as an aqueous emulsion, and can be typically a thermosetting plastic. In order to activate the latex, the latex emulsion contains a suitable curing agent or cross-linking agent, and after the web is coated, the latex can be typically cured to effect cross-linking. For example, curing is accomplished by passing the coated web e.g. through a hot air oven or through an air drier 42, where the temperature can typically range from about 100° C. to 260° C., but this depends upon the specific type of latex resin used, upon the curing agent or cross-linking agent, upon the amount of latex, the thickness of the web, the degree of vacuum, and the machine speed.

Typically alter the curing step, i.e. downstream the oven or drier 42, the web 12 is further conveyed by a second screen 44 operating about rollers 60, 61, 62, and 63 towards second dispensing means 46 where a latex binder is provided also to the second surface 8 of the web 12. The second dispensing means 46 can typically be completed by a second suction box 48 and an oven or drier 50, where in turn the second latex coating can be likewise cured by heating typically in the same temperature range.

In general, according to a typical embodiment of the present invention, the airlaid sheet material should not substantially comprise any thermal bonding, i.e., substantially no bonding from either partial or total fusion of the synthetic fibres. Of course this would not exclude thermosetting of the latex binder, and the temperature of the curing steps should be accordingly set.

According to the present invention, the latex binder is provided to the first surface 6 of the web 12 by the dispensing means 40 in a first amount, and to the second surface 8 of the web 12 by the dispensing means 46 in a second amount, wherein the ratio of the first amount to the second amount is typically from 2:1 to 4:1, or also from 2.5:1 to 3.5:1. The amounts can be for example expressed in mass units, although the final selected ratio is independent of the units.

The resulting absorbent fibrous structure 10 exiting from the last oven now exhibits sufficient integrity and can be cut, rolled, packaged, etc.

The airlaid sheet material 10 obtainable by the process of the present invention, namely the web 12, comprises cellulosic and synthetic fibres, for example a uniform blend of randomly distributed cellulosic and synthetic fibres, and is substantially free of superabsorbent material. The cellulosic fibres can include fibres such as wood pulp and cotton fibres, as well as modified celluiosic fibres such as rayon and cellulose acetate. Typically, the celluiosic fibres in the airlaid sheet material 10 are wood pulp fibres. According to the present invention the celluiosic fibres are comprised in the airlaid sheet material 10 in a relatively reduced amount, typically from 1% by weight to 30% by weight or from 1% by weight to 20% by weight, or also from 1% by weight to 10% by weight.

The synthetic fibres can include polyethylene, polypropylene, polyester, nylon fibres, bicomponent fibres, and the like. Typically the synthetic fibres can be constituted by polyethylene terephthalate fibres and/or polypropylene fibres. For example, polyethylene terephthalate fibres can be provided in the desired blend with cellulose fibres onto a nonwoven carrier layer of polypropylene fibres. According to the present invention, the airlaid sheet material 10 can comprise from 45% by weight to 98% by weight of synthetic fibres, or from 65% by weight to 94% by weight, or also from 80% by weight to 94% by weight of synthetic fibres.

The synthetic fibres, which can be provided in any length including staple length, can typically contribute to the strength of the structure. They can also be treated to make them hydrophilic, in order not to decrease the absorbent capacity of the airlaid sheet material of the present invention.

The airlaid sheet material 10 obtainable by the process of the present invention comprises the latex binder in an amount from 1% by weight to 25% by weight, or from 5% by weight to 15% by weight, or also from 5% by weight to 10% by weight.

All percentages are calculated on the dry weight of the airlaid sheet material, and refer to the overall composition of the airlaid sheet material of the present invention, i.e., both in the case where the airlaid sheet material comprises a single layer typically formed by means of a single distributor, and also when the airlaid sheet material comprises multiple plies or layers formed by different distributors and possibly having different compositions. Said percentages also comprise the optional carrier layer, when present.

The latex binder can be typically provided as an aqueous emulsion or dispersion, which may contain different percentages of solids. Latex binders can be readily available from several manufacturers.

Because the latex emulsions are water miscible, they may be further diluted. If desired, before being applied to the web. Also, latex compositions can be typically thermosetting, and in order to effect cross-linking, they contain a small amount of a suitable cross-linking agent which are well known chemical agents for this purpose, such as N-methylolacrylamide. Any type of latex known in the art which is suitable for fibrous structures can be used fro the airlaid sheet material of the present invention. Latices available are classified by chemical family, and those particularly useful include vinyl acetate and acrylic ester copolymers, ethylene vinyl acetate copolymers, styrene butadiene carboxylate copolymers, and polyacrylonitriles, and sold, for example, under the trade names of Airbond, Airflex and Vinac of Air Products, Inc., Hycar and Geon of Goodrich Chemical Co., and Folatex of H. B. Fuller Company.

According to the present invention, typically the airlaid sheet material 10 obtainable by the process described above comprises substantially no thermal bonding, i.e., substantially no bonding from either partial or total fusion of the synthetic fibres. Of course this does not exclude thermosetting of the latex binder.

According to the present invention, the airlaid sheet material 10 obtainable by the above described process can have a basis weight from 50 g/m$^2$ to 400 g/m$^2$, or from 60 g/m$^2$ to 200 g/m$^2$.

The airlaid sheet material 10 of the present invention obtainable by the process as described above is illustrated in FIG. 2. The airlaid sheet material 10 can comprise a web 12 of randomly distributed fibres 14, and a latex binder 16, 16', 18, 18', which provides a coating, schematically indicated in the drawing by a shading 16, 18, onto respective first and second surfaces 6, 8 of the airlaid sheet material 10, and which has also penetrated or impregnated the web 12 to a certain degree 16', 18' and has partially coated some of the fibres.

Figure 2:
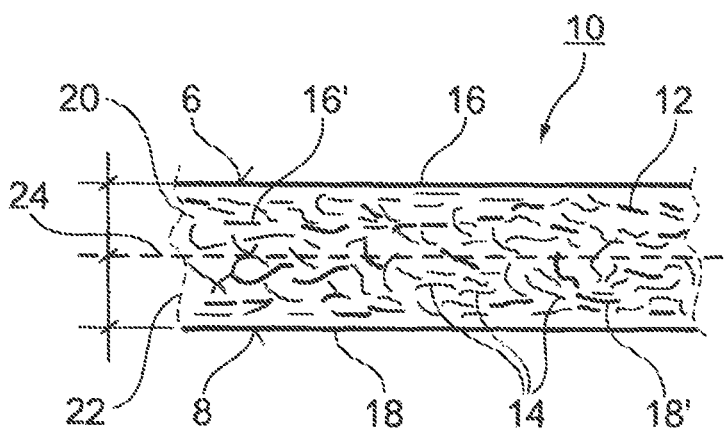
FIG. 2 is an enlarged, cross-sectional view of an airlaid sheet material according to the present invention.

In the airlaid sheet material 10 obtainable by the process of the present invention the portion in the thickness direction of the airlaid sheet material can be divided in a first region 20 and in a second region 22 by a plane 24, indicated as a dashed line in FIG. 2, which is perpendicular to the thickness direction of the airlaid sheet material 10, and in turn typically parallel to both the outer first and second surfaces 6 and 8 thereof. According to the present invention, the amount of latex binder in the first region 20 of the airlaid sheet material 10 is from 2 to 4 times the amount of latex in the second region 22, or also from 2.5 to 3.5 times the amount of latex in the second region 22. The ratios can be calculated for example from respective basis weights of the latex binder in the first and second region 20, 22, for example being expressed in grams per square meter, or also as absolute amounts in grams, of course when the respective first and second region 20, 22 refer to a same area of the airlaid sheet material 10. The amounts or the basis weights of the latex in the two regions can be evaluated with methods known in the art, such as tor example microscopic inspection, FTIR spectroscopy, thermogravimetric analysis.

Without being bound to any theory, it is believed that the airlaid sheet material 10 obtainable by the process according to the present invention provides good acquisition and retention capacity tor body fluids, owing to the combination of features described above. In particular, the relatively low amount of celluiosic fibres and the corresponding high percentage of synthetic fibres, typically for example of polyethylene terephthalate fibres, combined with the substantial lack of superabsorbent material, provides for a very good handling towards body fluids, for example menses and blood, with an improved capacity of handling and distributing the fluid, owing to the stable fibrous structure not subject to collapse upon fluid absorption, and also not prone to gel blocking, owing to the substantial lack of superabsorbent material.

In addition, the specific distribution of the latex material within the thickness of the airlaid sheet material provides the airlaid sheet material with an improved stability, but still with a particular softness and flexibility, which translates into an improved comfort for the user.

Notwithstanding the latex coating, airlaid sheet materials 10 obtainable by the process of the present invention are soft yet strong and absorbent, exhibiting a relatively high tensile strength.

The airlaid sheet material 10 of the present invention can be part of the core of a hygiene absorbent article, or can be also constitute the absorbent core of such an article.

When the airlaid sheet material 10 of the present invention is incorporated into a hygienic absorbent article such as tor example a sanitary napkin or pantiliner, the first surface 6 and the first region 20 can be typically oriented towards the garment facing surface of the absorbent article, i.e., the surface which is meant to face the user's garment when worn, while the second surface 8 and the second region 22 are consequently oriented towards the body facing surface of the absorbent article. This exemplary orientation of the airlaid sheet material 10 within an absorbent article also provides for an even better fluid acquisition capacity, in addition to structure stability, as the region of the airlaid sheet material containing relatively less latex binder is facing the user, hence is meant to first receive the fluid, and takes advantage of the more "open" structure provided by the relatively lesser amount of latex among the fibres.

In general, the airlaid sheet materials of this invention can be suitably used for incontinent pads, diaper core, diaper insert, and also for surgical and wound bandages, providing absorbent capacity.

The airlaid sheet material of the present invention can also comprise further components, such as for example odour control agents, in order to control unpleasant odours associated with the fluids that can contact them.

Each dimension for which a value is defined herein is a technical dimension, which, in the context of the present invention is not to he understood literal. Hence, all embodiments having dimensions functionally equivalent to the dimensions stated herein are intended to be covered by the scope of the invention, e.g. a dimension of "40 mm" has to be understood as meaning "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that is alone, or in any combination with any other reference or references, teaches, suggests or discloses any such invention. Further, to the extend that arm meaning or definition of term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An airlaid sheet material obtainable by the process comprising the steps of:
   providing a fibrous web comprising cellulosic fibres and synthetic fibres, and having a first surface and a second surface, and
   applying a latex binder to said first surface and to said second surface of said fibrous layer, respectively in a first amount and in a second amount, with a ratio of said first amount to said second amount from 2:1 to 4:1,
   said airlaid sheet material comprising
   from 1% to 30% by weight of sale celluiosic fibres,
   from 1% to 25% by weight of said latex binder.

2. An airlaid sheet material according to claim 1, wherein said airlaid sheet material comprises from 45% to 98% by weight of said synthetic fibres.

3. An airlaid sheet material according to claim 1, wherein said synthetic fibres are selected among polyester, polyethylene, polypropylene, nylon, bicomponent fibres.

4. An airlaid sheet material according to claim 1, wherein said synthetic fibres are polyethylene terephthalate fibres and/or polypropylene fibres.

5. An airlaid sheet material according to claim 1, wherein said airlaid sheet material comprises substantially no thermal bonding.

6. An airlaid sheet material according to claim 1, wherein said airlaid sheet material has a basis weight from 50 $g/m^2$ to 400 $g/m^2$.

7. An airlaid sheet material according to claim 1, wherein said cellulosic fibres and said synthetic fibres are provided as a uniform blend.

8. An airlaid sheet material according to claim 1, wherein, when the portion in the thickness direction of said airlaid sheet material is divided in a first and a second region by a plane perpendicular to said thickness direction of said sheet material, and corresponding to one half of said thickness, the amount of latex binder in said first region is from 2 to 4 times the amount of latex binder in said second region.

9. An absorbent article comprising an airlaid sheet material according to claim 1, and having a body facing surface and a garment facing surface, wherein said first region of said airlaid sheet material is oriented towards said garment facing surface, and said second region of said airlaid sheet material is oriented towards said body facing surface.

\* \* \* \* \*